United States Patent [19]
Hoshi et al.

[11] Patent Number: 5,214,267
[45] Date of Patent: May 25, 1993

[54] APPARATUS FOR CONTROLLING HEATER FOR HEATING OXYGEN SENSOR

[75] Inventors: Kouichi Hoshi, Susono; Makoto Suzuki, Mishima, both of Japan

[73] Assignee: Toyota Jidosha Kabushiki Kaisha, Toyota, Japan

[21] Appl. No.: 625,897

[22] Filed: Dec. 11, 1990

[30] Foreign Application Priority Data

Dec. 15, 1989 [JP] Japan ................... 1-325205

[51] Int. Cl.⁵ ............................................. H05B 1/02
[52] U.S. Cl. ................................. 219/497; 219/494
[58] Field of Search ............... 219/494, 497, 501, 504; 123/434, 676, 685, 697; 204/425, 424

[56] References Cited

U.S. PATENT DOCUMENTS

| | | | |
|---|---|---|---|
| 4,319,451 | 3/1982 | Tajima | 123/676 |
| 4,471,648 | 9/1984 | Uchida | 123/697 |
| 4,500,412 | 2/1985 | Takahashi | 204/425 |
| 4,510,036 | 4/1985 | Takeuchi | 204/425 |
| 4,524,264 | 6/1985 | Takeuchi | 219/497 |
| 4,561,402 | 12/1985 | Nakano | 123/697 |
| 4,563,991 | 1/1986 | Akatsuka | 123/697 |
| 4,708,777 | 11/1987 | Kuraoka | 204/424 |
| 4,721,088 | 1/1988 | Mieno | 123/697 |
| 4,993,392 | 2/1991 | Tanaka | 204/425 |

FOREIGN PATENT DOCUMENTS

| | | |
|---|---|---|
| 197459 | 3/1982 | Japan . |
| 164241 | 5/1985 | Japan . |

Primary Examiner—Teresa J. Walberg
Attorney, Agent, or Firm—Kenyon & Kenyon

[57] ABSTRACT

An apparatus for controlling a heater for heating an oxygen sensor provided in an exhaust gas flow passage of an internal combustion engine disposed in an automotive vehicle, includes an operating condition detecting unit for detecting a predetermined operating condition of the internal combustion engine, and a resistance/power detection unit for detecting a heater resistance value of the heater and an amount of power supplied to the heater when the internal combustion engine is in the predetermined operating condition. The apparatus also includes a power control unit for comparing the heater resistance value detected by the resistance/power detection unit with a target resistance value and for supplying the heater with power supplied from a battery in a definite-resistance control mode in which the heater resistance value is controlled to become equal to the target resistance value, a resistance value correction unit for correcting the target resistance value so that a difference between the amount of power detected by the resistance/power detection unit and a standard amount of power becomes equal to zero, and a storage unit for storing the target resistance value corrected by the resistance value correction unit as a learning value. Further, the apparatus includes a storage state judgment unit for judging whether or not the the learning value is correctly stored in the storage unit, and a stop unit for stopping the power control unit to supply the heater with power in the definite-resistance control mode.

12 Claims, 8 Drawing Sheets

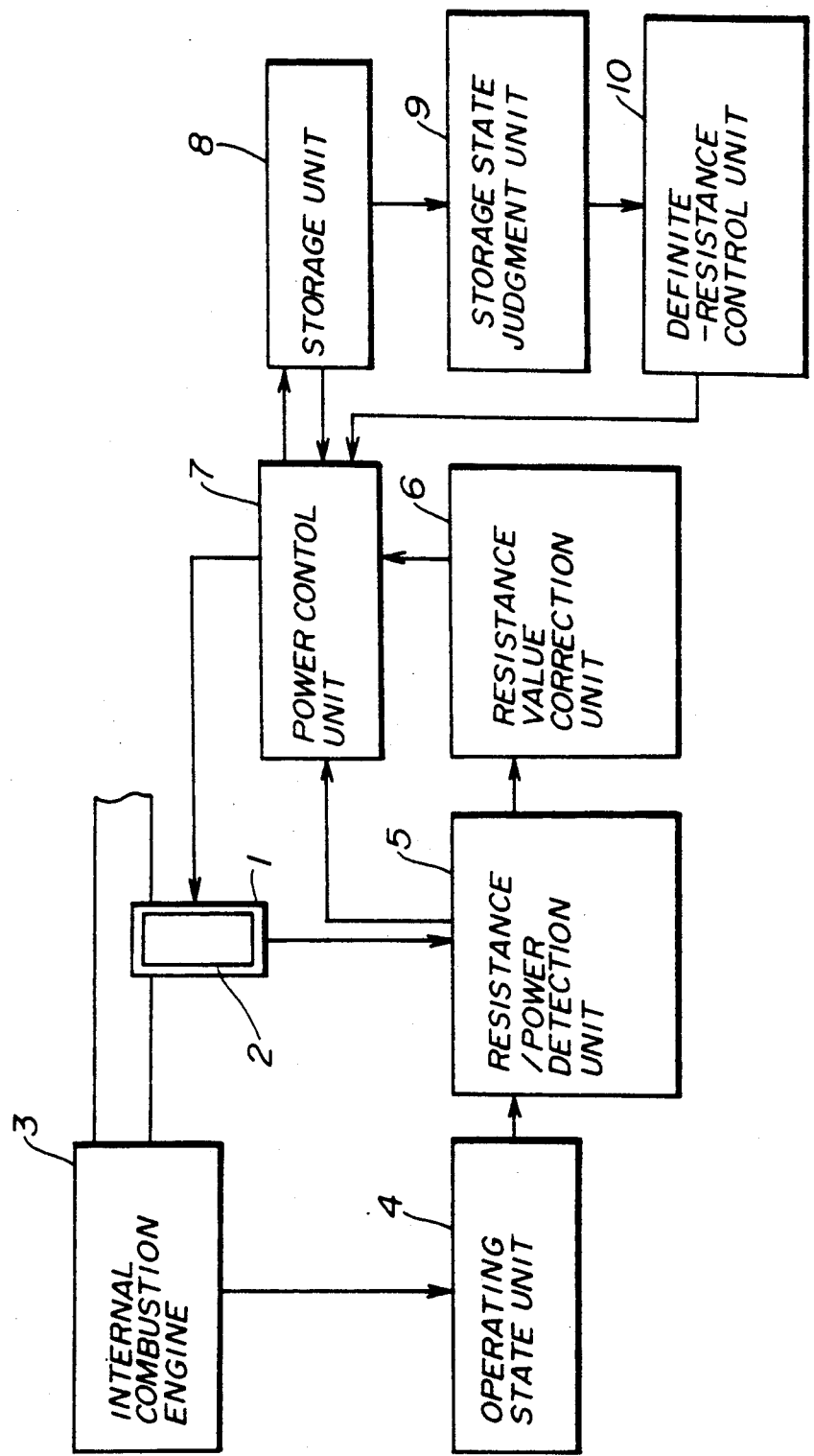

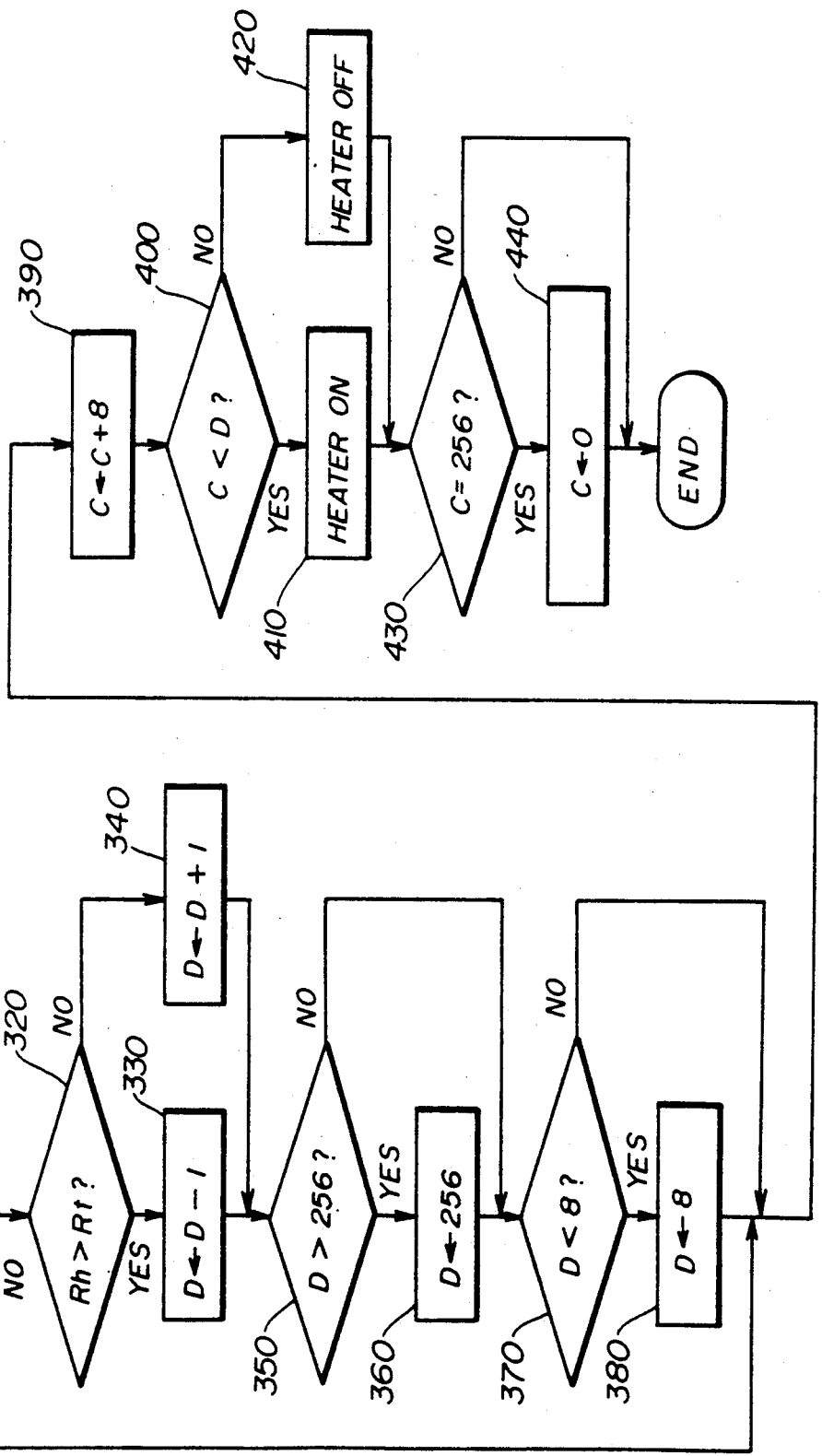

APPARATUS FOR CONTROLLING HEATER FOR HEATING OXYGEN SENSOR

BACKGROUND OF THE INVENTION (1) Field of the Invention

The present invention generally relates to an apparatus for controlling a heater for heating an oxygen sensor used in an internal combustion engine for measuring an air-fuel ratio in an exhaust gas. More particularly, the present invention is concerned with an apparatus for learning a target heater resistance and controlling the temperature of the oxygen sensor on the basis of the learned target heater resistance.

(2) Description of Related Art

Recently, various control devices have been developed which are directed to improving the output power of an internal combustion engine, reducing fuel consumption or clarifying exhaust gas. Such control devices employ oxygen sensors without exception. As is well known, an oxygen sensor is used for measuring the concentration of an oxygen component contained in the exhaust gas. An oxygen sensor has a sensor element (sense portion) formed of a solid electrolyte or a semiconductor. An output signal of the oxygen sensor depends on the temperature of the sensor element thereof.

It is known that an oxygen sensor having a sensor element made of titania ($TiO_2$) has an air-fuel ratio (A/F) characteristic as a temperature function of the sensor element as shown in the graph of FIG. 1. The vertical axis of the graph represents the air-fuel ratio, and the horizontal axis thereof represents the temperature of the sensor element. A stoichiometric air-fuel ratio exists between air-fuel ratios $a_1$ and $a_2$. When the actual air-fuel ratio is equal to or smaller than the air-fuel ratio $a_1$ (a rich air-fuel ratio), a large amount of hydro carbon (HC) is contained in the exhaust gas. In contrast, when the actual air-fuel ratio is equal to or larger than the air-fuel ratio $a_2$ (a lean air-fuel ratio), a large amount of nitric oxide ($NO_x$) is contained in the exhaust gas. It can be seen from the graph of FIG. 1 that the temperature of the sensor element must be regulated so that it is maintained within the narrow temperature range between T1 and T2 so that the air-fuel ratio of the titania oxygen sensor can be kept within the narrow range between $a_1$ and $a_2$ including the stoichiometric air-fuel ratio.

With the above in mind, a conventional oxygen sensor is equipped with a heater, which is subjected to a power supply control so that the value of resistance of the heater becomes equal to a definite resistance value. When the resistance value of the heater is regulated at the definite resistance value, the temperature of the sensor element is also regulated at a constant temperature. Such a power supply control is disclosed in Japanese Laid-Open Patent Application Nos. 57-197459, 60-164241 or 60-202348, for example.

As is well known, the resistance values for different heaters built in oxygen sensors are different from each other. In other words, the resistance values of heaters are within a certain resistance range. This fact causes an error in the temperature control of the oxygen sensor. In order to cancel an error in the temperature control of the oxygen sensor arising from variations in the resistance values of heaters, one may consider that the temperature of the oxygen sensor is controlled by a learning control. During the learning control, the supply of power to the heater is controlled so that the heater resistance value becomes equal to a target resistance value. When an internal combustion engine is in a predetermined stable operating condition, the target resistance value is stored, as a learning value, in a storage unit, such as a battery backup random access memory (hereafter simply referred to as a battery backup RAM). The temperature control is carried out based on the learning value.

By employing the learning control of the heater for the oxygen sensor, it becomes possible to individually determine the target resistance values of the respective heaters on the basis of the respective actual resistance values of the heaters. As a result, it becomes possible to compensate for variations in the heater resistance values.

As has been described above, the target resistance value is stored in the storage unit, such as the battery backup RAM, and used for the future temperature control of the heater. In this case, there is a problem which has to be solved. When the learning value stored in the storage unit is destroyed due to, for example, the battery installed in the vehicle is exchanged for another one. After a new battery is mounted on the vehicle, the target resistance value of the heater is set to an initial resistance value. On the other hand, the temperature characteristic of the oxygen sensor will vary due to variations in the heater resistance value as well as deterioration due to the age of the heater. In this case, the initial resistance value will greatly deviate from an appropriate resistance value based on the present condition of the heater. Due to this fact, it becomes very difficult to precisely detect the oxygen density in the vicinity of the oxygen sensor and precisely set the air-fuel ratio to the ideal air-fuel ratio by an air-fuel ratio feedback control. These problems further cause a catalyzer exhaust stench and deteriorate drivability.

SUMMARY OF THE INVENTION

It is a general object of the present invention to provide an improved apparatus for controlling a heater for an oxygen sensor in which the above-mentioned disadvantages are eliminated.

A more specific object of the present invention is to provide an apparatus capable of precisely controlling a heater for an oxygen sensor even when the learning value obtained by the learning control is destroyed.

The above-mentioned objects of the present invention are achieved by an apparatus for controlling a heater for heating an oxygen sensor provided in an exhaust gas flow passage of an internal combustion engine disposed in an automotive vehicle, comprising an operating condition detecting unit for detecting a predetermined operating condition of the internal combustion engine, a resistance/power detection unit for detecting a heater resistance value of the heater and an amount of power supplied to the heater when the internal combustion engine is in the predetermined operating condition, and a power control unit, coupled to the resistance/power detection unit and the heater, for comparing the heater resistance value detected by the resistance/power detection unit with a target resistance value and for supplying the heater with power supplied from a battery in a definite-resistance control mode in which the heater resistance value is controlled to become equal to the target resistance value. The apparatus also comprises a resistance value correction unit, coupled to the resistance/power detection unit and the power control unit, for correcting the target resistance value so that a difference between the amount of power detected by the resistance/power detection unit and a standard amount of power becomes equal to zero, and a storage unit, coupled to the resistance value correction unit, for storing the target resistance value corrected by the resistance value correction unit as a learning value. Further, the apparatus comprises a storage state judgment unit, coupled to the storage unit, for judging whether or not the learning value is correctly stored in the storage unit, and a stop unit, coupled to the power control unit and the storage state judgment unit, for stopping the power control unit to supply the heater with power in the definite-resistance control mode.

BRIEF DESCRIPTION OF THE DRAWINGS

FIG. 2 is a block diagram illustrating an outline of a heater control apparatus according to the present invention;

FIG. 7 is a flowchart illustrating a definite-resistance resistance feedback control executed during the procedure shown in FIG. 6;

DESCRIPTION OF THE PREFERRED EMBODIMENTS

Figure 1:
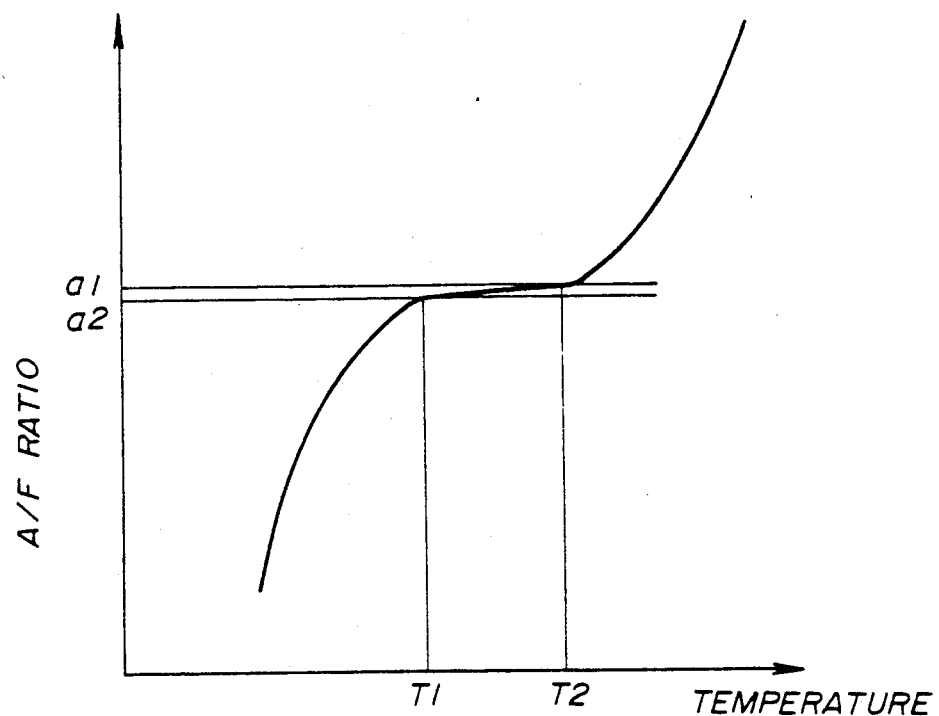
FIG. 1 is a graph illustrating the relationship between the temperature of a sensor element of an oxygen sensor and the actual air-fuel ratio.

A description will now be given of an outline of the present invention with reference to FIG. 2. The apparatus shown in FIG. 2 is composed of an operating condition judgment unit 4, a resistance/power detection unit 5, a resistance value correction unit 6, a power control unit 7, a storage unit 8, a storage state judgment means 9, and a definite-resistance feedback control stop unit 10. The operating condition judgment unit 4 determines whether or not an internal combustion engine 3 is in a predetermined operating condition. The resistance/power detection unit 5 detects a resistance value of a heater 2 provided for an oxygen sensor 1 fastened to an exhaust gas flow passage, and a power amount supplied to the heater 2, when the operating condition judgment unit 4 determines that the internal combustion engine 3 is working in the predetermined operating condition. The resistance value correction unit 6 compares the power amount detected by the resistance/power detection unit 5 with a standard amount of amount, and corrects a target resistance value of the heater 2 on the basis of the comparison result so that the difference between the detected power amount and the standard power amount becomes zero. The power control unit 7 supplies the heater 2 with power controlled based on the target resistance value corrected by the resistance correction unit 6, so that a definite-resistance feedback control (which will be described in detail later) is realized. The storage unit 8 stores the corrected target resistance value as a learning value. The storage state judgment means 9 judges whether or not the learning value is correctly stored in the storage unit 8. The definite-resistance feedback control stop unit 10 causes the power control unit 7 to stop the definite-resistance feedback control when the storage state judgment means 9 detects that the learning value is not correctly stored in the storage unit 8.

If the learning value stored in the storage unit 8 has been destroyed for a certain reason (exchanging of a battery), the storage state judgment means 9 detects this fact, and generates a detection signal. In response to the detection signal, the definite-resistance feedback control stop unit 10 outputs a control signal to the power control unit 7 and thereby causes the power control unit 7 to stop the definite-resistance feedback control. As the learning proceeds, the learning value can correct variations in the heater resistance value as well as deterioration due to age more definitely. However, a target resistance value obtained immediately after the learning value has been destroyed is not mainly based on variations in the heater resistance value. For this reason, when the heater is supplied with power based on such a target resistance value, it is impossible to set the oxygen sensor 1 at an appropriate temperature. According to the present invention, the power control unit 7 is instructed to stop the definite-resistance feedback control when the learning value stored in the storage unit 8 is destroyed. As a result, it becomes possible to prevent the heater control, based on the target resistance value which has not yet been corrected sufficiently, from being executed and thus prevent the temperature of the oxygen sensor 1 from increasing to an abnormally high temperature or decreasing to an abnormally low temperature.

Figure 3:
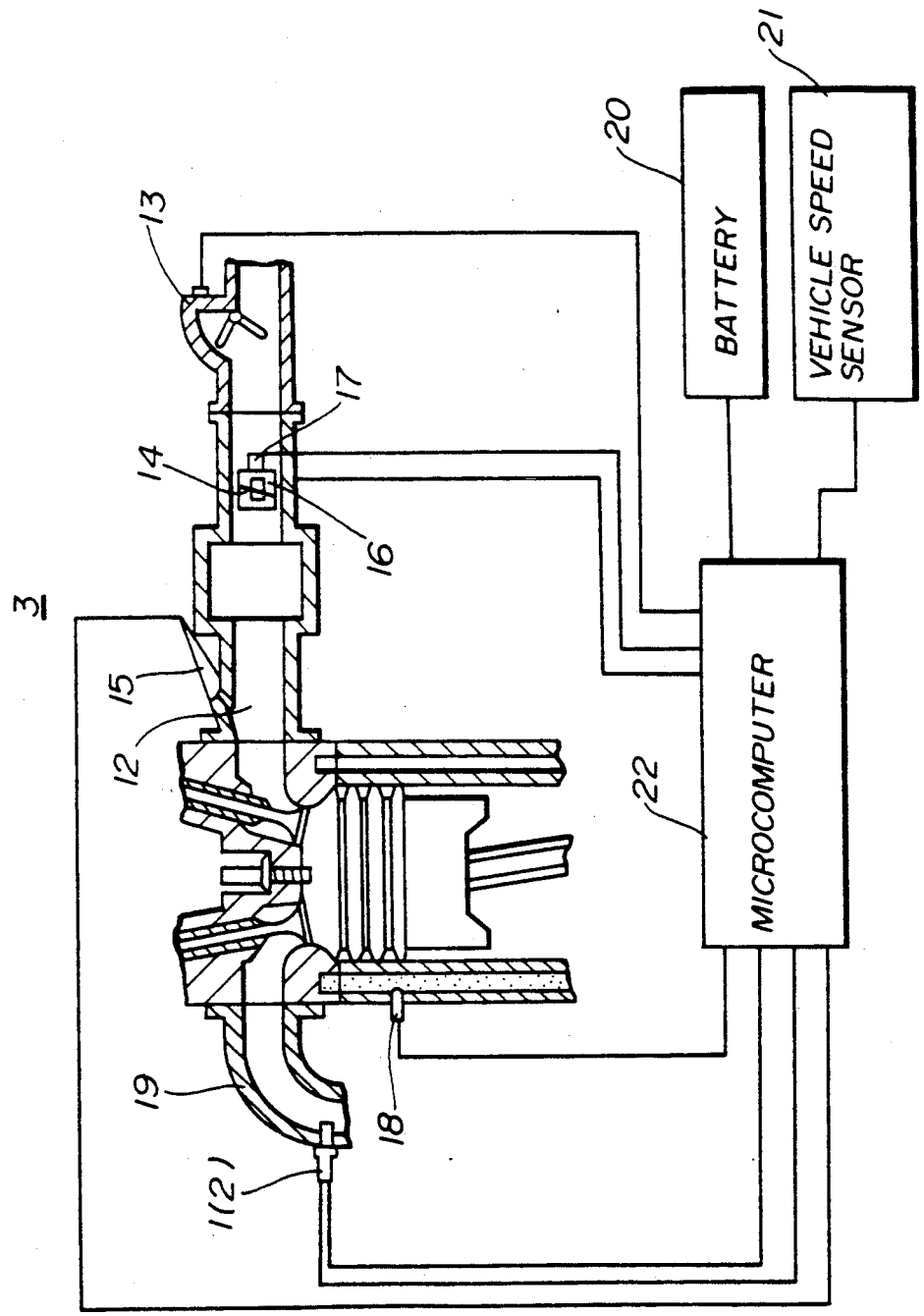
FIG. 3 is a diagram illustrating a heater control apparatus applied to an internal combustion engine according to the present invention.

A description will now be given of a preferred embodiment of the present invention. Referring to FIG. 3, there is illustrated a heater control apparatus applied to the internal combustion engine 3 according to the preferred embodiment of the present invention. The internal combustion engine 3 (hereafter simply referred to as an engine) is formed of, for example, a four-cycle spark ignition engine disposed in an automotive vehicle. The engine 3 has an air-intake passage 12, to which an airflow meter 13, a throttle valve 14 and an injector 15 are mounted in this order from an upstream side of the air passage. The airflow meter 13 directly measures the amount of air taken into the engine 3. The airflow meter 13 includes a potentiometer, which generates an analog voltage signal in proportion to the amount of air flowing into the air-intake passage 12. The throttle valve 14 cooperates with an accelerator pedal (not shown for the sake of simplicity), and is in a completely closed state when the engine 3 is in an idle state. As the load of the engine 3 increases, the throttle valve 14 is opened at a larger angle. The throttle valve 14 has a potentiometer 16, which generates a voltage in proportion to an opening angle of the throttle valve 14. An idle switch 17, which is provided for the throttle valve 14, outputs a detection signal when the throttle valve 14 is in the completely closed state. The injector 15 is located at an air-intake port, and opens its valve when it is supplied with electricity. When the valve of the injector 15 is in the open state, a pressurized fuel supplied from a fuel tank (not shown) via a fuel pump (also not shown) is injected into the air-intake port.

A coolant temperature sensor 18 for measuring the temperature of a coolant is disposed in a cylinder block of the engine 3. The coolant temperature sensor 18 outputs an analog voltage signal based on the temperature of the coolant. Provided in an exhaust gas flow passage 19 is an oxygen ($O_2$) sensor 1 for detecting the concentration of an oxygen component in an exhaust gas from the cylinder of the engine 3. The oxygen sensor 1 has a heater 2 and a sensor element sensitive to the oxygen component. The heater 2 is supplied with electrical power controlled by a heater control device 11 (which will be described later).

A battery 20 functions as a power source which drives a starter motor (not shown for the sake of simplicity), and supplies a battery backup RAM 26 (FIG. 4), which will be described later. The contents of the battery backup RAM 29 are saved even when the engine 3 is not operating. A vehicle speed sensor 21 generates a signal representative of a vehicle speed based on the revolutions of a shaft (not shown) coupled to a vehicle shaft.

Connected to a microcomputer 22 are the oxygen sensor 1, the heater 2, the airflow meter 13, the injector 15, the potentiometer 16, the idle switch 17, the coolant temperature sensor 18, the battery 20 and the vehicle speed sensor 21. The microcomputer 22 receives signals output by the sensors and executes various controls so that the engine 3 operates correctly.

Figure 4:
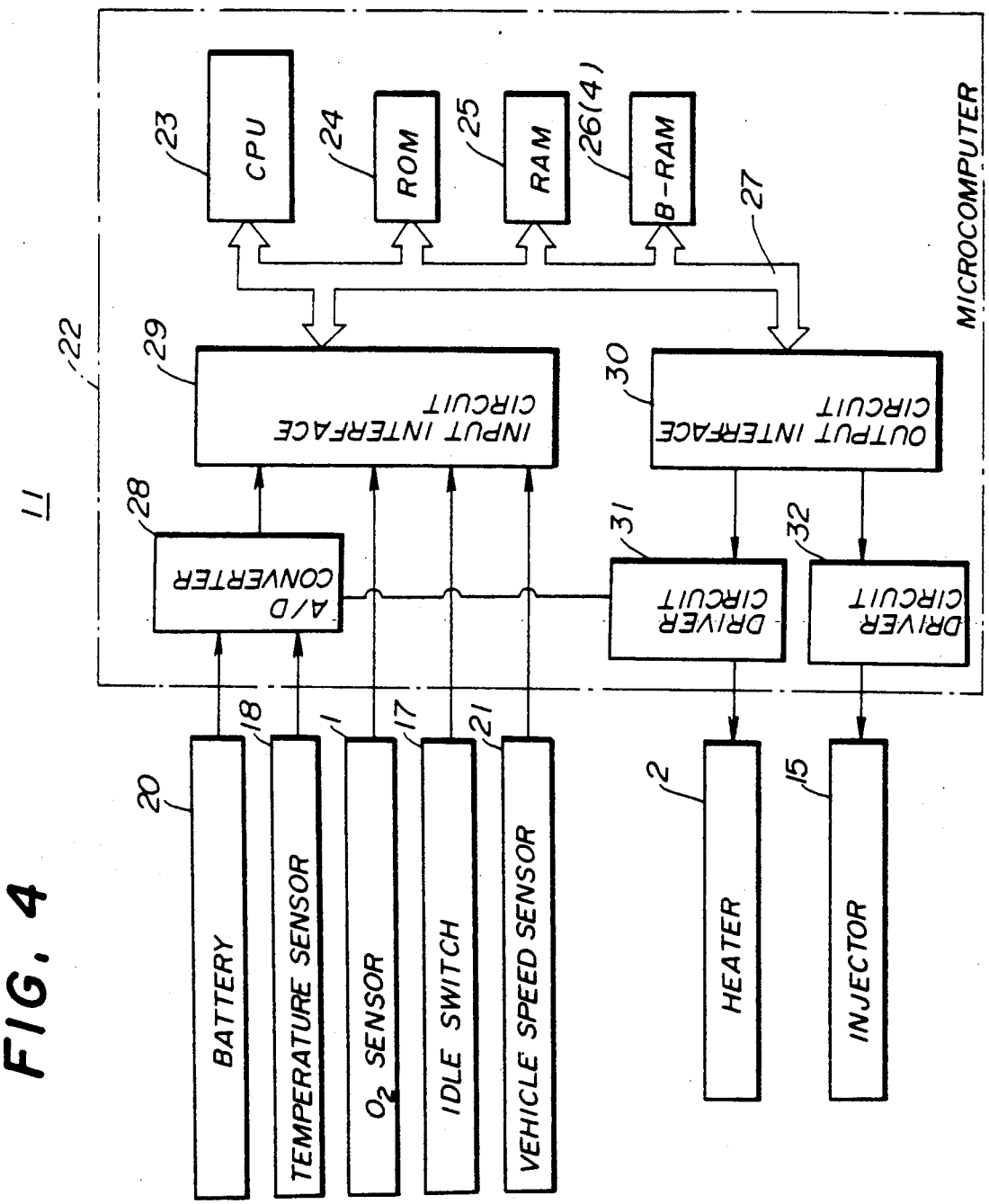
FIG. 4 is a block diagram of an electrical system of the heater control apparatus shown in FIG. 3.

Referring to FIG. 4, there is illustrated an electrical structure of the heater control apparatus according to the preferred embodiment of the present invention. In FIG. 4, those parts which are the same as those shown in the previous figures are given the same reference numerals. The microcomputer 22 is composed of a central processing unit (hereafter simply referred to as a CPU) 23, a read only memory (hereafter simply referred to as a ROM) 24, a RAM 25, the aforementioned battery backup RAM (B-RAM) 26, an input interface circuit 29 and an output interface circuit 30, all of which are mutually connected via a bidirectional bus 27. Further, the microcomputer 22 has an analog-to-digital converter (hereafter simply referred as an A/D converter) 28, and two driver circuits 31 and 32. The A/D converter 28 is connected to the input interface circuit 29, and the two driver circuits 31 and 32 are connected to the output interface circuit 30.

The analog voltage signals respectively output by the battery 20 and the coolant temperature sensor 18 are input to the A/D converter 28, which respectively outputs corresponding digital signals. These digital signals are supplied to the bus 27 via the input interface circuit 29. Further, the A/D converter 28 is supplied with an output signal from the driver circuit 31. The input interface circuit 29 is also supplied with an oxygen concentration detection signal output by the oxygen sensor 1, an idle signal output by the idle switch 17 and a vehicle speed signal output by the vehicle speed sensor 21, all of which are transferred to the bus 27 via the input interface circuit 29. On the other hand, electrical power is supplied to the heater 2 from the battery 20 via the output interface circuit 30 and the driver circuit 31. The injector 15 is supplied with a fuel injection signal from the CPU 23 via the bus 27, the output interface circuit 30 and the driver circuit 32.

Figure 5:
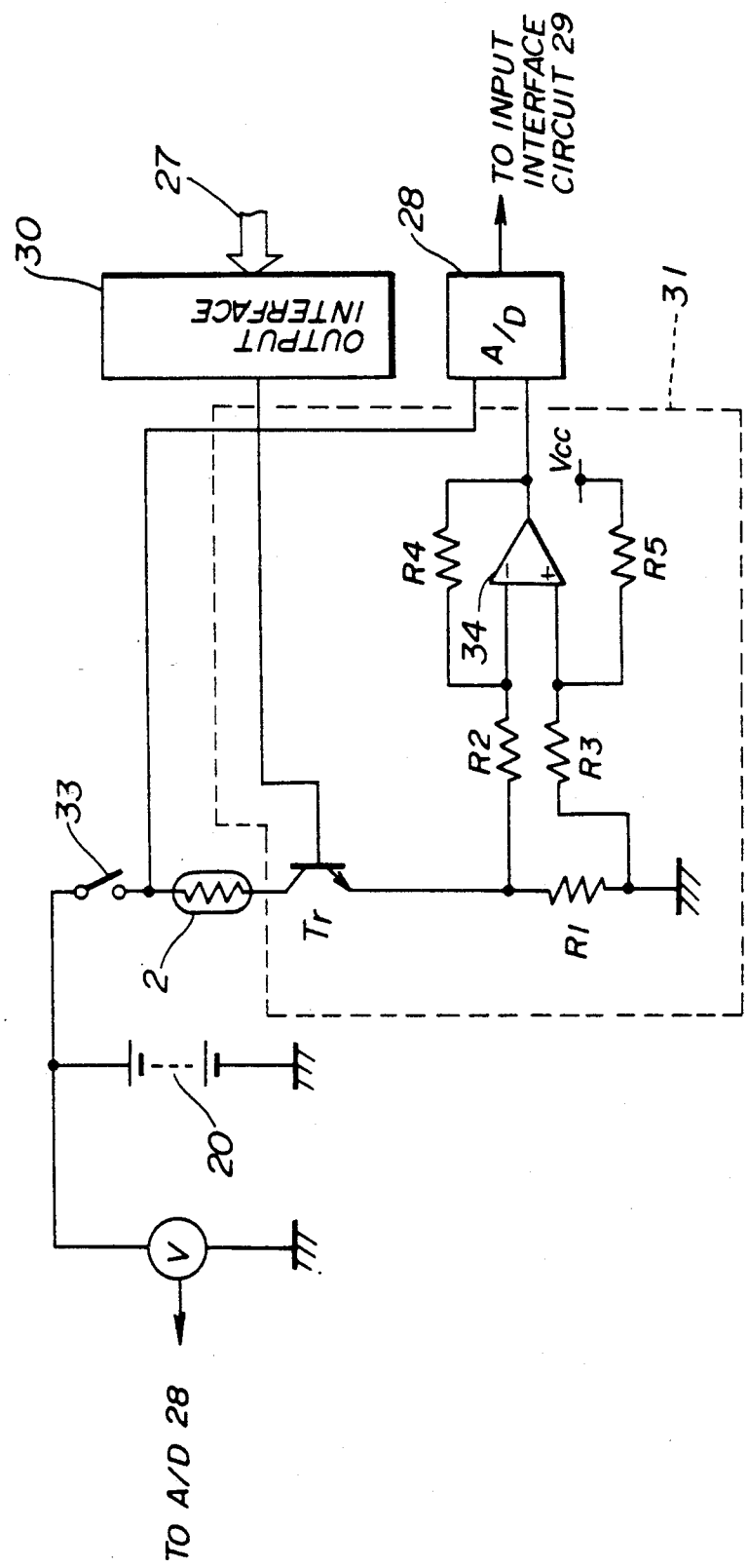
FIG. 5 is a circuit diagram of a driving circuit coupled to a heater shown in FIG. 4.

Referring to FIG. 5, there is illustrated a driver circuit 31 and its peripheral circuits. A positive terminal of the battery 20 is connected to one end of the heater 2 via an ignition switch 33. The driver circuit 31 has a driving transistor Tr having a collector connected to the other end of the heater 2, an emitter grounded via a resistor R1, and a base connected to the output interface circuit 30. Also, the driver circuit 31 has resistors R2, R3, R4 and R5, and an operational amplifier 34. A potential difference corresponding to a voltage drop developed across the resistor R1 is applied to inverting and non-inverting input terminals of the operational amplifier 34 through the resistors R2 and R3. An output terminal of the operational amplifier 34 is coupled to the inverting input terminal via the resistor R4. The non-inverting input terminal of the operational amplifier 34 is pulled up to a positive potential Vcc via the resistor R5.

The microcomputer 22 realizes the resistance/power detection unit 5, the resistance value correction unit 6, the power control unit 7, the storage state detection unit 9 and the definite-resistance feedback control stop unit 10 shown in FIG. 2 by means of software (program). A description will now be given of the operation of the microcomputer 22 with reference to FIG. 6.

Figure 6:
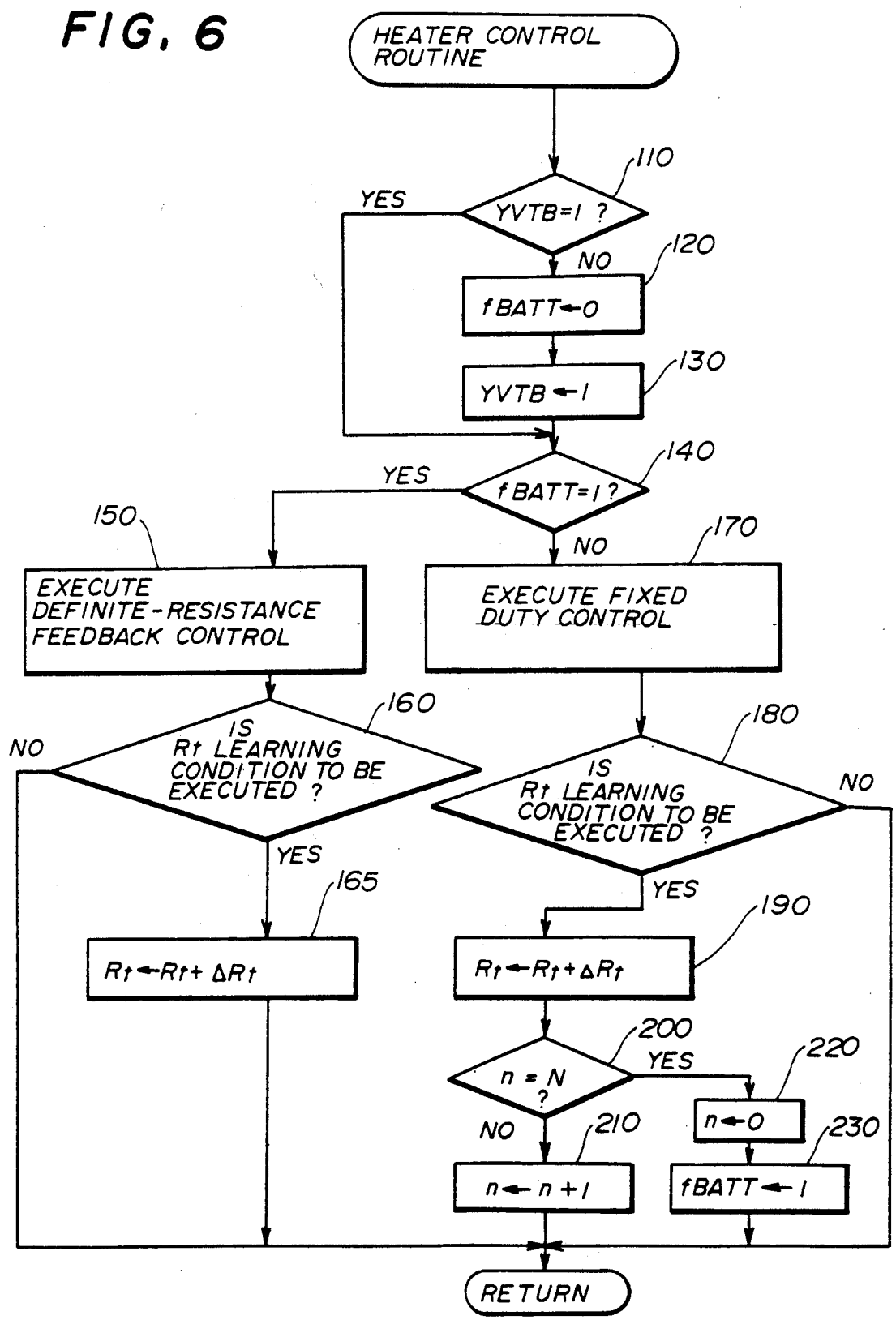
FIG. 6 is a flowchart illustrating the operation of the heater control apparatus shown in FIGS. 3 and 4.

Referring to FIG. 6, there is illustrated a heater control routine (procedure) executed by the microcomputer 22. The routine shown in FIG. 6 is executed for every 16 ms, for example. The routine commences with step 110, at which step the CPU 23 determines whether or not a flag YVTB is equal to 1. The flag YVTB is reset to zero when the supply of electrical power from the battery 20 is substantially stopped. For example, the flag YVTB is reset when the drivability of the battery 20 decreases, the battery 20 is exchanged for a new one, or a short-circuit occurs. When it is determined, at step 110, that YVTB=1, the CPU 23 concludes that the supplying of electrical power has been substantially stopped. It will be noted that the flag YVTB is reset when the supplying of electrical power is temporarily stopped and is then started again. When the engine 3 is not operating and the supply of electrical power is stopped, the contents of the battery backup RAM 26 shown in FIG. 4 are destroyed. As a result, a learning value obtained by executing the definite-resistance feedback control (which will be described later) is also destroyed.

When it is determined, at step 110, that YVTB=0, the CPU 23 resets a battery flag $f_{BATT}$ to zero at step 120, and sets the flag YVTB to 1 at step 130. It will be noted that the status where $f_{BATT}=0$ indicates that the learning value stored in the battery backup RAM 26 has been destroyed, and the status where $f_{BATT}=1$ indicates that the learning value is correctly stored therein. On the other hand, when the result obtained at step 110 is YES, the CPU 23 executes step 140. In this case, there is no problem regarding the battery power supply.

At step 140, the CPU 23 judges whether or not the battery flag $f_{BATT}$ is equal to 1. The judgment procedure at step 140 is carried out to determine whether or not the learning value is correctly stored in the battery backup RAM 26. When it is determined, at step 140, that $f_{BATT}=1$, the CPU 23 executes the definite-resistance feedback control at step 150.

A description will now be given of the definite-resistance feedback control (mode) executed at step 150, with reference to FIG. 7. The definite-resistance feedback control procedure shown in FIG. 7 is executed for every predetermined period, for example, 16 ms.

The CPU 23 commences to execute step 310, at which step it is determined whether or not a heater resistance value Rh of the heater 2 is equal to a heater target resistance value Rt obtained at step 165 (FIG. 6), which step will be described later. The heater resistance value Rh is calculated each time the step 150 (FIG. 6) is executed. The heater resistance value Rh can be obtained by the following formula:

$$Rh = (Vb/Vc - 1) \cdot Rc$$

where Vb is the voltage of the battery 20, Vc is the voltage drop developed across the resistor R1 shown in FIG. 5, and Rc is the resistance value of the resistor R1. When the result obtained at step 310 is YES, the CPU 23 executes step 390. On the other hand, when the result at step 310 is NO, the CPU 23 executes step 320, at which step it is determined whether or not $Rh > Rt$. When $Rh > Rt$, the CPU 23 decreases a duty counter D (which is a software or program counter) by 1 at step 330. On the other hand, when it is determined that $Rh \leq Rt$, the CPU 23 increases the duty counter D by +1. The value of the duty counter D denotes the number of counts corresponding to a duty ratio in pulse-like power supplied to the heater 2. At step 350, the CPU 23 determines whether or not $D > 256$. A maximum pulse width of the driving signal applied to the base of the transistor Tr shown in FIG. 5 corresponds to 256. Thus, the heater 2 is supplied with electricity during a period corresponding to the duty ratio to the maximum count value, 256. However, in actual practice, the duty ratio is limited so that it is always in excess of 8. In this case, the duty ratio is controlled within the range between 3.125% and 100%. Steps 350, 360, 370 and 380 are provided for limiting the duty ratio so that it is greater than 8.

The CPU 23 determines, at step 350, whether or not $D > 256$. When the result at step 350 is YES, step 360 is executed and, on the other hand, when the result is NO, step 370 is executed. At step 360, the CPU 23 inserts 256 into the duty counter D. At step 370, the CPU 23 determines whether or not $D < 8$. When the result at step 370 is YES, step 380 is executed and, on the other hand, when the result at step 370 is NO, step 390 is executed. At step 380, the CPU 23 inserts 8 into the duty counter D.

At step 390, the CPU 23 increases the value of a flow counter C by 8. The flow counter C increases its counter value by 8 each time the procedure (flow) shown in FIG. 7 is executed for every 16 ms, and returns to zero when the counter value becomes equal to 256. In this case, the counter value in the flow counter C becomes equal to 256 for every 512 ms. At step 400, the CPU 23 determines whether or not $C < D$. When the result at step 400 is YES, the heater 2 is turned ON at step 410. On the other hand, when the result at step 400 is NO, the heater 2 is turned ON at step 420. At step 430, the CPU 23 determines whether or not $C = 256$. When the result at step 420 is YES, the flow counter C is reset to zero at step 440. On the other hand, when the result at step 430 is NO, the procedure shown in FIG. 7 ends.

In short, the definite-resistance feedback control calculates the heater resistance value Rh, and controls the amount of power supplied to the heater 2 so that the heater resistance value Rh becomes equal to the target resistance value Rt obtained at this time. It will be noted that the target resistance value Rt varies on the basis of the operating condition of the engine 3, or the peripheral environment of the oxygen sensor 1. Thus, a correction value ΔRt used at step 165 is calculated on the basis of the amount of power supplied to the heater 2. The target resistance value Rt being currently used is renewed by feeding back the correction value ΔRt thereto, so that the heater 2 can be controlled in accordance with the operating condition of the engine 3. As a result, the preciseness of the oxygen concentration signal output by the oxygen sensor 1 is improved, and the air-fuel ratio can be controlled more precisely.

Figure 8:
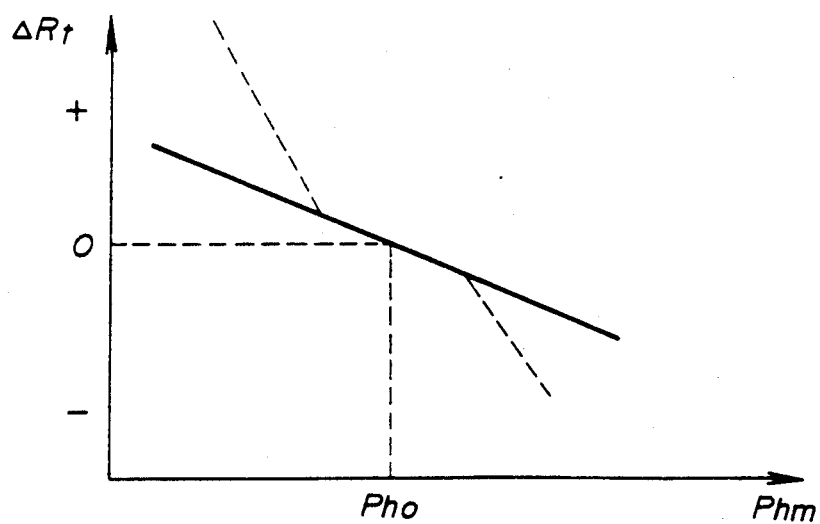
FIG. 8 is a graph illustrating the relationship between a correction value and a deviation between an average amount of power supplied to the heater and a standard amount of power.

More specifically, the correction value ΔRt can be obtained as follows. The first step is to calculate an average amount Phm of power which has been supplied to the heater for a predetermined period (equal to, for example 512 ms). On the other hand, the ROM 24 or the battery backup RAM 24 stores information showing the relationship between the correction value ΔRt and the amount of power which is to be supplied to the heater 2. In FIG. 8, Pho denotes a standard amount of power. The correction value ΔRt with respect to the target resistance value Rt is calculated from a deviation between the standard amount of power Pho and the average amount of power Phm. The straight solid line shown in FIG. 8 shows a basic change in the correction value ΔRt with respect to the deviation between the standard amount of power Pho and the average amount of power Phm. When Pho=Phm, the correction value ΔRt is zero. The correction value ΔRt is a positive value when Phm<Pho, and negative value when Phm>Pho. As the deviation between Pho and Phm decreases toward zero in a state where Phm<Pho, the positive correction value ΔRt decreases. On the other hand, as the deviation between Pho and Phm decreases toward zero in a state where Phm>Pho, the negative correction value ΔRt decreases. It is also possible to define the correction value ΔRt, as shown by a broken line in FIG. 8. A change in the correction value ΔRt is small around the standard amount of power Pho, and large when the average amount of power Phm greatly deviates from the standard amount of power Pho.

The learning control has not yet been executed immediately after the engine 3 is fabricated. Thus, it is necessary to predetermine the target resistance value Rt of the heater 2. As has been described previously, the resistance values of different oxygen sensors are different from each other. Thus, it is necessary to determine the initial target resistance value Rt so that the oxygen sensors are prevented from having abnormally high or low temperatures.

Figure 9:
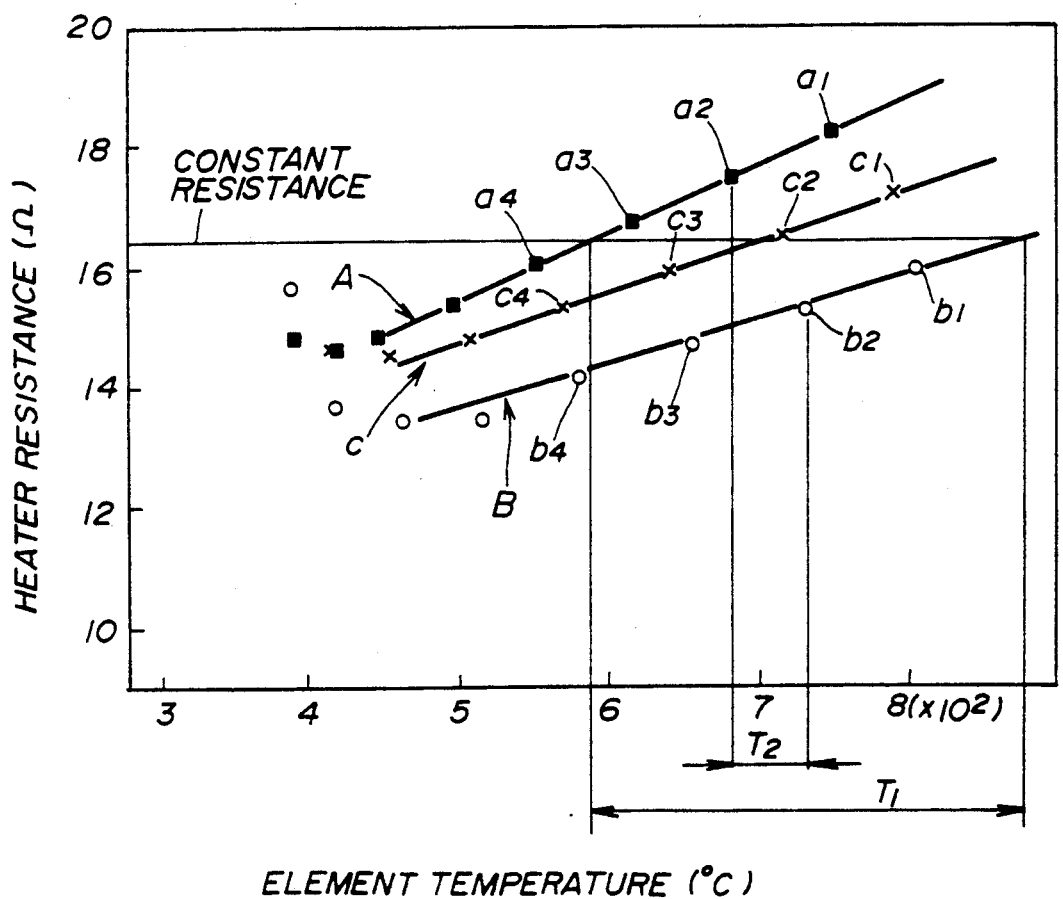
FIG. 9 is a graph illustrating the relationship between the heater resistance value and the temperature of an oxygen sensitive element of an oxygen sensor.

FIG. 9 is an experimental graph illustrating the relationship between the heater resistance and the temperature of the oxygen sensitive element of the oxygen sensor. A curve A indicates an upper limit resistance value, B indicates a lower limit resistance value, and C is an average resistance value. In order to prevent the oxygen sensor 1 from having abnormally high or low temperatures, it is desirable to set the constant resistance value to be a value around the average resistance value and set the temperature of the oxygen sensitive element to be an intermediate temperature between the upper limit temperature and the lower limit temperature. For example, the graph of FIG. 9 shows that the average resistance value for 700° C. is about 16.2 ohms. This definite-resistance value is stored in the ROM 24 beforehand.

Turning now to FIG. 6, after the CPU 23 executes the definite-resistance feedback control at step 150, it determines, at step 160, whether or not the engine 3 is in an Rt learning execution condition. The Rt learning execution condition corresponds to an idling state in which the idle switch 17 is ON, the vehicle speed detected by the vehicle speed sensor 21 is equal to or less than 5 km, and the coolant temperature detected by the coolant temperature sensor 18 is equal to or lower than 70° C. The engine 3 is stable in the idling state. In this state, the peripheral environment of the oxygen sensor 1 is also stable. It is also possible to define the Rt learning execution condition by another engine state.

When it is determined, at step 160, that the Rt learning execution condition is satisfied, the CPU 23 calculates, at step 165, the correction value ΔRt by the aforementioned way, and renews the target resistance value Rt by inserting the correction value ΔRt into the current target resistance value Rt. The renewed target resistance value Rt is stored in the battery backup RAM 26 for the next execution of step 150. Thus, the definite-resistance feedback control is executed, using the target resistance value obtained by the previous learning control at step 150. As a result, it is possible to precisely control the oxygen sensor 1 and compensate for variations in the heater resistance values. After step 165 is executed, the procedure ends.

On the other hand, when it is determined, at step 140, that the battery flag $f_{BATT}$ is zero, that is, when it is determined that the learning value stored in the battery backup RAM 26 has been destroyed, at step 170, the CPU 23 stops the execution of the definite-resistance feedback control (step 150) and executes a fixed duty control.

The fixed duty control (mode) is defined as follows. A pulse-like current is supplied to the heater 2. The duty ratio indicates ratio of the heater ON period to one period of the pulse current. In the fixed duty control, the heater 2 is driven in the state where the duty ratio is fixed. It will be noted that when the duty ratio is 100%, the heater 2 is continuously supplied with current.

If the definite-resistance feedback control is executed in the state where the learning value stored in the battery backup RAM 26 has been destroyed, it becomes impossible to precisely control the temperature of the oxygen sensor 1 because the past correction data obtained during the procedure for compensating for a variation in the resistance value of the heater 2 has been lost. In this case, there is a possibility that the oxygen sensor 1 will be set to an abnormally high or low temperature by the definite-resistance feedback control and thus be prevented from outputting an erroneous oxygen concentration greatly different from the actual oxygen concentration. For the above-mentioned reason, the definite-resistance feedback control is stopped, and the fixed duty control is executed.

A description will now be given of how to determine the fixed duty ratio with reference to FIG. 9. In FIG. 9, $a_1$, $b_1$ and $c_1$ are the upper limit resistance value, the lower limit resistance value, and the average resistance value, respectively, when the duty ratio is 100%. Similarly, $a_2$, $b_2$ and $c_2$ are the upper limit resistance value, the lower limit resistance value, and the average resistance value, respectively, when the duty ratio is equal to 88%. Similarly, $a_3$, $b_3$ and $c_3$ are the upper limit resistance value, the lower limit resistance value, and the average resistance value, respectively, when the duty ratio is equal to 77%. Similarly, $a_4$, $b_4$ and $c_4$ are the upper limit resistance value, the lower limit resistance value, and the average resistance value, respectively, when the duty ratio is equal to 50%. It is desirable to select an intermediate value between the upper and lower limit values in order to determine the fixed duty ratio, as in the case when determining the constant resistance of the heater 2. When the temperature of the oxygen sensor 1 is equal to 700° C., the upper limit resistance value $a_2$, the lower limit resistance value $b_2$ and the average resistance value $c_2$ are closest to 700° C. Thus, the fixed duty ratio is set to be equal to 88%. The fixed duty ratio thus obtained is stored in the battery backup RAM 24 beforehand.

By carrying out the fixed duty control, it is possible to control the temperature of the oxygen sensor 1 so that it falls in a narrow temperature range. Assuming that a fixed resistance value is selected in place of the fixed duty ratio control and power is supplied to the heater 2, the oxygen sensor 1 is set to a temperature in a temperature range T1. That is, a large error in the setting of the temperature of the oxygen sensor 1 occur. On the other hand, by carrying out the fixed duty control, the temperature of the oxygen sensor 1 falls in a temperature range T2 which is narrower than the temperature range T1. Thus, by carrying out the fixed duty control, it becomes possible to precisely control the temperature of the oxygen sensor 1 and thus precisely obtain the oxygen concentration, as compared with the case where the fixed heater resistance value is used. As a result, it is possible to obtain a smaller difference between the oxygen concentration detected by the oxygen sensor 1 and the actual oxygen concentration.

Turning again to FIG. 6, after executing the fixed duty ratio control at step 170, the CPU 23 determines, at step 180, whether or not the aforementioned Rt learning execution condition is satisfied. When the result at step 180 is YES, the CPU 23 calculates the correction value ΔRt on the basis of the fixed duty ratio, and inserts the correction value ΔRt into the learning value Rt at step 190. As has been described previously, the target resistance value used at step 165 is the immediately previous learning value. On the other hand, since the learning value used when step 190 is executed has been destroyed, the aforementioned fixed resistance value is read out from the ROM 24 and used as the target resistance value Rt. The renewed target resistance value Rt obtained at step 190 is stored in the battery backup RAM 26.

The learning value obtained after it is determined, at step 140, that the battery flag $f_{BATT}$ is equal to 1, is stored in the battery backup RAM 26 for the first time as the learning value. At this time, there is a possibility that this learning value will not be sufficient to compensate for the variation in the heater resistance value. For this reason, the definite-resistance feedback control is not started until the learning at step 190 is repeatedly carried out a predetermined number of times (N times). In other words, the definite-resistance feedback control is not carried out until the learning is sufficiently carried out. The CPU 23 determines whether or not n=N at step 200 where n is the value in a counter, and executes step 210 when the result at step 200 is NO. At step 210, the counter value n is incremented by 1, and the procedure ends. On the other hand, when it is determined, at step 200, that n=N, the counter value n is reset to zero at step 220, and the battery flag $f_{BATT}$ is reset to zero at step 230. After the learning has been carried out sufficiently, the heater 2 is controlled by the definite-resistance feedback control.

In the above-mentioned embodiment of the present invention, the CPU 23 detects the fact that the learning value in the battery backup RAM 26 has been destroyed by determining whether or not the power supply from the battery 20 is stopped. Alternatively, as shown in FIG. 5, it is possible to connect a voltage meter V to the battery 20 and reset the battery flag $f_{BATT}$ to zero when an output signal of the voltage meter has become equal to or less than a predetermined level. It is also possible to provide the learning value with a parity bit and determine whether or not the learning value has been destroyed by checking the parity bit.

The present invention is not limited to the specifically disclosed embodiments, and variations and modifications may be made without departing from the scope of the present invention.

What is claimed is:

1. An apparatus for controlling a heater for heating an oxygen sensor provided in an exhaust gas flow passage of an internal combustion engine disposed in an automotive vehicle, said apparatus comprising:

operating condition detecting means for detecting a predetermined operating condition of said internal combustion engine;

resistance/power detection means for detecting a heater resistance value of said heater and an amount of power supplied to said heater when said internal combustion engine is in said predetermined operating condition;

power control means, coupled to said resistance/power detection means and said heater, for comparing said heater resistance value detected by said resistance/power detection means with a target resistance value and for supplying said heater with power supplied from a battery in a definite-resistance control mode in which said heater resistance value is controlled to become equal to said target resistance value;

resistance value correction means, coupled to said resistance/power detection means and said power control means, for correcting said target resistance value so that a difference between the amount of power detected by said resistance/power detection means and a standard amount of power becomes equal to zero;

storage means, coupled to said resistance value correction means, for storing said target resistance value corrected by said resistance value correction means as a learning value;

storage state judgment means, coupled to said storage means, for judging whether or not said learning value is correctly stored in said storage means; and stop means, coupled to said power control means and said storage state judgment means, for stopping said power control means from supplying said heater with power in said definite-resistance control mode.

2. An apparatus as claimed in claim 1, wherein said storage state judgment means comprises means for determining whether or not the power supply from said battery is interrupted and for concluding that said learning value is not correctly stored in said storage means when it is determined that the power supply from said battery is interrupted.

3. An apparatus as claimed in claim 1, wherein said storage state judgment means comprises means for determining whether or not a voltage of said battery is equal to or less than a predetermined voltage and for concluding that said learning value is not correctly stored in said storage means when it is determined that the voltage of said battery is equal to or less than said predetermined voltage.

4. An apparatus as claimed in claim 1, wherein said power control means comprises fixed duty cycle control means for supplying said heater with power from said battery in a fixed duty cycle control mode in which the power is supplied to said heater by allowing a pulse current from said battery to pass through said heater at a fixed duty ratio when said storage state judgment means judges that said learning value is not correctly stored in said storage means.

5. An apparatus as claimed in claim 4, further comprising learning means for repeatedly learning said target resistance when said internal combustion engine is in said predetermined operating condition in the state where the power is supplied to said heater in said fixed duty control mode and for controlling said power control means to operate in said definite-resistance control mode instead of said fixed duty control mode when a predetermined number of times that said target resistance has been learned.

6. An apparatus as claimed in claim 1, wherein said power control means comprises means for supplying said heater with a reduced amount of power when said heater resistance value is greater than said target resistance value and for supplying said heater with an increased amount of power when said heater resistance value is smaller than said target resistance value.

7. An apparatus as claimed in claim 1, wherein said resistance value control means comprises means for renewing said target resistance value by a correction value based on the difference between the amount of power detected by said resistance/power detection means and the standard amount of power.

8. An apparatus as claimed in claim 7, further comprising means for increasing said correction value as a deviation obtained by subtracting said amount of power detected by said resistance/power detection means from said standard amount of power increases.

9. An apparatus as claimed in claim 7, further comprising means for decreasing said correction value as a deviation obtained by subtracting said standard amount of power from said amount of power detected by said resistance/power detection means increases.

10. An apparatus as claimed in claim 1, wherein said storage means comprises a battery backup random access memory.

11. An apparatus as claimed in claim 1, wherein said operating condition detecting means comprises means for detecting an idle state of said internal combustion engine.

12. An apparatus as claimed in claim 1, wherein said oxygen sensor detects a concentration of an oxygen component contained in said exhaust gas flow passage.

* * * * *